US010345200B2

(12) United States Patent
Scialo et al.

(10) Patent No.: US 10,345,200 B2
(45) Date of Patent: Jul. 9, 2019

(54) MICROBIAL AIR SAMPLER INTEGRATING MEDIA PLATE AND SAMPLE COLLECTION DEVICE

(71) Applicant: Particle Measuring Systems, Inc., Boulder, CO (US)

(72) Inventors: Giovanni Scialo, Salerno (IT); Ronald W. Adkins, Erie, CO (US); Davide Recchia, Fonte Nuova (IT)

(73) Assignees: PARTICLE MEASURING SYSTEMS, S.R.L., Rome (IT); PARTICLE MEASURING SYSTEMS, INC., Boulder, CO (US)

( * ) Notice: Subject to any disclaimer, the term of this patent is extended or adjusted under 35 U.S.C. 154(b) by 171 days.

(21) Appl. No.: 14/338,615

(22) Filed: Jul. 23, 2014

(65) Prior Publication Data

US 2015/0075301 A1 Mar. 19, 2015

Related U.S. Application Data

(60) Provisional application No. 61/953,128, filed on Mar. 14, 2014.

(30) Foreign Application Priority Data

Jul. 23, 2013 (IT) .......................... RM201300128 U

(51) Int. Cl.
*G01N 1/22* (2006.01)
*G01N 21/95* (2006.01)
(Continued)

(52) U.S. Cl.
CPC ......... *G01N 1/2208* (2013.01); *G01N 1/2273* (2013.01); *G01N 21/9515* (2013.01);
(Continued)

(58) Field of Classification Search
CPC ........... G01N 1/02; G01N 1/22; G01N 1/2208
See application file for complete search history.

(56) References Cited

U.S. PATENT DOCUMENTS 3,001,914 A 9/1961 Andersen
3,938,366 A 2/1976 Wertlake et al.
(Continued)

FOREIGN PATENT DOCUMENTS

CN 102220235 A 10/2011
EP 1175990 A1 1/2002
(Continued)

OTHER PUBLICATIONS

Particle Measuring Systems. 'DualCapt'. Datasheet, 2008. Retrieved online. [Retrieved on Oct. 6, 2014]. <URL:www.kenelec.eom.au/sitebuilder/products/files/279/dual_capt.pdf>.
(Continued)

*Primary Examiner* — David Z Huang
(74) *Attorney, Agent, or Firm* — Leydig, Voit & Mayer, Ltd.

(57) ABSTRACT

The invention generally provides devices and methods for sampling, detecting and/or characterizing particles, for example, via collection, growth and analysis of viable biological particles such as microorganisms. Devices and methods of the invention include particle samplers and impactors for collecting and/or analyzing biological particles in manufacturing environments requiring low levels of particles, such as cleanroom environments for electronics manufacturing and aseptic environments for manufacturing pharmaceutical and biological products, such as sterile medicinal products. Devices and methods of the invention incorporate an integrated sampler and impact surface, such as the receiving surface of a growth media, in a manner to minimize, or entirely eliminate, risks associated with user handling, such as the occurrence of false positive determi-
(Continued)

nations due to contamination of the impact surface during particle sampling, growth or analysis processes.

20 Claims, 11 Drawing Sheets

(51) Int. Cl.
*C12M 1/22* (2006.01)
*C12M 1/00* (2006.01)
*C12M 1/12* (2006.01)
(52) U.S. Cl.
CPC ............ *C12M 23/10* (2013.01); *C12M 23/38* (2013.01); *C12M 37/04* (2013.01)

(56) References Cited

U.S. PATENT DOCUMENTS

| | | |
|---|---|---|
| 4,594,715 A | 6/1986 | Knollenberg |
| 4,798,465 A | 1/1989 | Knollenberg |
| 4,893,928 A | 1/1990 | Knollenberg |
| 5,032,721 A | 7/1991 | Bacon et al. |
| 5,095,206 A | 3/1992 | Bacon, Jr. et al. |
| 5,234,838 A | 8/1993 | Bacon, Jr. |
| 5,282,151 A | 1/1994 | Knollenberg |
| 5,283,199 A | 2/1994 | Bacon, Jr. et al. |
| 5,671,046 A | 9/1997 | Knowlton |
| 5,693,895 A | 12/1997 | Baxter |
| 5,726,753 A | 3/1998 | Sandberg |
| 5,751,422 A | 5/1998 | Mitchell |
| 5,805,281 A | 9/1998 | Knowlton et al. |
| 5,861,950 A | 1/1999 | Knowlton |
| 5,889,589 A | 3/1999 | Sandberg |
| 5,903,338 A | 5/1999 | Mavliev et al. |
| 6,167,107 A | 12/2000 | Bates |
| 6,246,474 B1 | 6/2001 | Cerni et al. |
| 6,275,290 B1 | 8/2001 | Cerni et al. |
| 6,472,203 B1 * | 10/2002 | Gallup .................. C12M 23/10 435/305.4 |
| 6,615,679 B1 | 9/2003 | Knollenberg et al. |
| 6,709,311 B2 | 3/2004 | Cerni |
| 6,859,277 B2 | 2/2005 | Wagner et al. |
| 6,903,818 B2 | 6/2005 | Cerni et al. |
| 6,945,090 B2 | 9/2005 | Rodier |
| 7,030,980 B1 | 4/2006 | Sehler et al. |
| 7,088,446 B2 | 8/2006 | Cerni |
| 7,088,447 B1 | 8/2006 | Bates et al. |
| 7,208,123 B2 | 4/2007 | Knollenberg et al. |
| 7,235,214 B2 | 6/2007 | Rodier et al. |
| RE39,783 E | 8/2007 | Cerni et al. |
| 7,456,960 B2 | 11/2008 | Cerni et al. |
| 7,576,857 B2 | 8/2009 | Wagner |
| 7,667,839 B2 | 2/2010 | Bates |
| 7,796,255 B2 | 9/2010 | Miller |
| 7,916,293 B2 | 3/2011 | Mitchell et al. |
| 7,973,929 B2 | 7/2011 | Bates |
| 7,985,949 B2 | 7/2011 | Rodier |
| 8,027,035 B2 | 9/2011 | Mitchell et al. |
| 8,154,724 B2 | 4/2012 | Mitchell et al. |
| 8,174,697 B2 | 5/2012 | Mitchell et al. |
| 8,427,642 B2 | 4/2013 | Mitchell et al. |
| 8,800,383 B2 | 8/2014 | Bates |
| 2005/0028593 A1 | 2/2005 | Rodier |
| 2007/0269849 A1 | 11/2007 | Bridenne et al. |
| 2009/0078862 A1 | 3/2009 | Rodier et al. |
| 2009/0190128 A1 | 7/2009 | Cerni et al. |
| 2009/0268202 A1 | 10/2009 | Wagner |
| 2010/0062415 A1 | 3/2010 | Schwoebel et al. |
| 2010/0212436 A1 | 8/2010 | Swenson et al. |
| 2011/0267451 A1 | 11/2011 | Drescher et al. |
| 2011/0301613 A1 | 12/2011 | Green |
| 2015/0075301 A1 | 3/2015 | Scialo et al. |

FOREIGN PATENT DOCUMENTS

| | | |
|---|---|---|
| JP | 2000337818 A | 12/2000 |
| WO | WO 96/05040 A1 | 2/1996 |
| WO | WO 02/24279 A1 | 3/2002 |

OTHER PUBLICATIONS

International Search Report and Written Opinion dated Nov. 6, 2014, for corresponding International Application No. PCT/US14/47759.
Biswas et al. (1984), "High-velocity inertial impactors," Environ. Sci. Technol. 18(8): 611-616.
Adriani et al. (Feb. 1993), "Combined System for Observations of Tropospheric and Stratospheric Thin Clouds", Journal of Atmospheric and Oceanic Technology, vol. 10, pp. 34-48.
Mitchell et al. (Sep. 1959), "Improved Cascade Impactor for . . . Measuring Aerosol Particle Sizes in air pollutants, commercial aerosols or cigarette smoke", Industrial and Engineering Chemistry, vol. 51, No. 9, pp. 1039-1042.
Extended European Search Report dated May 22, 2017, for European Patent Application No. 14829610.6.
Partial Supplemental European Search report dated Feb. 7, 2017, for European Patent Application No. 14829610.6.
Chinese Office Action, English translation, and search report, dated Mar. 14, 2018, for corresponding Chinese application No. CN 201400523873.
Japanese Office Action and English translation, dated Apr. 10, 2018, for corresponding Japanese application No. JP 2016-529852.
Chinese Second Office Action, English translation, dated Nov. 8, 2018, in Chinese application No. CN 201400523873.
European Examination Report, dated Jan. 2, 2019 in European application No. 14829610.6.
Japanese Final Rejection, English Translation, dated Feb. 5, 2019 in Japanese Application No. 2016-529852.
European Examination Report, dated May 8, 2019 in corresponding European application No. 14829610.6.

* cited by examiner

1000

```
Provide an impactor comprising: a sampling head comprising one or more
intake apertures for sampling a fluid flow containing particles; and an
impactor base operationally connected to receive at least a portion of the
fluid flow from the sampling head; the impactor base comprising an impact      — 1002
surface for receiving at least a portion of the particles in the fluid flow and
an outlet for exhausting the fluid flow; wherein the sampling head and the
impactor base are integrated components that engage to enclose the
impact surface
```

```
Sterilize the impactor in a fully assembled configuration wherein the
impact surface remains enclosed by the sampling head and impactor       — 1004
base during sterilization
```

```
Sample the fluid flow with the impactor, wherein particles    — 1006
in the fluid are received by the impactor surface
```

```
Grow at least a portion of the biological particles received by
the impact surface; wherein the growing step is carried out    — 1008
without disengaging the sampling head and the impactor base
```

```
Detect viable biological particles received    — 1010
by the impact surface
```

```
Optically characterize at least a portion of the particles without    — 1012
disengaging the sampling head and the impactor base
```

Figure 12

MICROBIAL AIR SAMPLER INTEGRATING MEDIA PLATE AND SAMPLE COLLECTION DEVICE

CROSS-REFERENCE TO RELATED APPLICATIONS

This application claims the benefit of priority from Italian Patent Application No. RM2013U000128, filed Jul. 23, 2013, and U.S. Provisional Patent Application No. 61/953,128, filed Mar. 14, 2014, each of which is hereby incorporated by reference in its entirety.

STATEMENT REGARDING FEDERALLY SPONSORED RESEARCH OR DEVELOPMENT

Not applicable.

BACKGROUND OF INVENTION

This invention is in the field of particle sampling, collection and analysis. The invention generally relates to devices and methods for sampling and characterizing particles in fluids including air and process chemicals (e.g., gases and liquids) for applications including the evaluation of contaminants in a range of cleanroom and manufacturing environments.

Cleanrooms and clean zones are commonly used in semiconductor and pharmaceutical manufacturing facilities. For the semiconductor industry, an increase in airborne particulate concentration can result in a decrease in fabrication efficiency, as particles that settle on semiconductor wafers will impact or interfere with the small length scale manufacturing processes. For the pharmaceutical industry, where this type of real-time efficiency feedback is lacking, contamination by airborne particulates and biological contaminants puts pharmaceutical products at risk for failing to meet cleanliness level standards established by the US Food and Drug Administration (FDA) and other foreign and international health regulatory agencies.

Standards for the classification of cleanroom particle levels and standards for testing and monitoring to ensure compliance are provided by ISO 14664-1 and 14664-2. Aerosol optical particle counters are commonly used to determine the airborne particle contamination levels in cleanrooms and clean zones, and liquid particle counters are used to optically measure particle contamination levels in process fluids. Where microbiological particles are a particular concern, such as in the pharmaceutical industry, not only is quantification of the number of airborne particles important, but characterizing the viability and identity of microbiological particles is also at issue. ISO 14698-1 and 14698-2 provide standards for evaluation of cleanroom and clean zone environments for biocontaminants.

Collection and analysis of airborne biological particles is commonly achieved using a variety of techniques including settling plates, contact plates, surface swabbing, fingertip sampling and impactor-based active air samplers. Cascade impactors have traditionally been used for collection and sizing of particles. In these devices, a series of accelerations and inertial impacts successively strip smaller and smaller particles from a fluid flow. Each stage of an inertial impactor operates on the principle that particles suspended in air can be collected by forcing a dramatic change in the direction of the particle-containing airflow, where the inertia of the particle will separate the particle from the airflow streamlines and allow it to impact on the surface. Biswas et al. describe the efficiency at which particles can be collected in a high velocity inertial impactor (*Environ. Sci. Technol.*, 1984, 18(8), 611-616).

In some cleanroom environments, retrieving size information from a particle impactor is not always necessary. In this case, a single stage active air sampling impactor system is sufficient to collect biological particle concentrations subject to subsequent detection and analysis. In an impactor-based active air sampler used for collection of biological particles, the impact/collection surface commonly comprises a growth medium, such as an agar plate, as would be used with other biological particle collection techniques. After the particles are collected onto the growth media surface, the media is incubated to allow the biological particles to reproduce. Once the colonies reach a large enough size, they can be identified and characterized, for example using microscopic imaging, fluorescence, staining or other techniques, or simply counted visually by eye or by image analysis techniques.

For these types of biological particle collection and analysis techniques, various operational aspects are important to ensure efficient collection, detection and analysis. For example, the collection efficiency may be of high importance, as failing to detect that biological particles are present in cleanroom air can result in the cleanroom environment having higher levels of contamination than detected. Upon determination that under counting has occurred, pharmaceutical products made in those environments can be identified as failing to meet required standards, potentially leading to costly product recalls. Similarly, failing to ensure that the viability of collected biological particles is maintained during the collection process will also result in under counting. Such a situation can arise, for example, if the collected biological particles are destroyed, damaged or otherwise rendered non-viable upon impact with the growth medium, such that the collected particles do not replicate during the incubation process and, therefore, cannot be subsequently identified.

On the opposite extreme, biological particle concentrations can be overestimated due to false positives. Over counting of this nature arises where a biological particle that is not collected from the cleanroom air, but is otherwise placed in contact with the growth medium, is allowed to replicate during the incubation process and is improperly identified as originating from the cleanroom air. Situations that contribute to false positives include failing to properly sterilize the growth medium and collection system prior to particle collection and improper handling of the growth medium by cleanroom personnel as it is installed into a particle collection system and/or removed from the particle collection system and placed into the incubator. Again, this can result in a pharmaceutical product being identified as failing to meet required standards. Without sufficient measures to identify false positives, such a situation can result in pharmaceutical products that actually meet the required standards, but are destroyed due to an overestimation of biological particle concentration in the cleanroom air indicating that the standards were not met.

There remains a need in the art for particle collection systems capable of achieving efficient sampling of biological particles. For example, particle collection systems are needed for cleanroom and manufacturing applications that provide high particle collection efficiencies while maintaining the viabilities of collected bioparticles. In addition, particle collection systems are needed for cleanroom and manufacturing applications that reduce the occurrence of false positive detection events.

SUMMARY OF THE INVENTION

The invention generally provides devices and methods for sampling, detecting and/or characterizing particles, for example, via collection, growth and analysis of viable biological particles, such as microorganisms. Devices and methods of the invention include particle samplers and impactors for collecting and/or analyzing biological particles in manufacturing environments requiring low levels of particles, such as cleanroom environments for electronics manufacturing and aseptic environments for manufacturing pharmaceutical, biological and medical device products, such as sterile medicinal products. Devices and methods of the invention incorporate an integrated sampler and impact surface, such as the receiving surface of a growth media, in a manner to minimize, or entirely eliminate, risks associated with user handling, such as the occurrence of false positive determinations due to contamination of the impact surface during particle sampling, growth or analysis processes.

In some aspects, the invention provides a particle impactor device having an integrated sampler and enclosed impact surface designed for single use and/or disposable use, thereby eliminating the costs and contamination risks involved with reuse. Particle impactor devices of the present invention having an integrated sampler and enclosed impact surface are capable of achieving effective sampling and growth of biological particles while minimizing the incidence for user contamination during handling and use. Particle impactor devices of the present invention having an integrated sampler and enclosed impact surface are also capable of effective sterilization in a fully assembled configuration wherein the impact surface, such as the receiving surface of a growth medium, is maintained in an enclosed configuration during the sterilization process, thereby eliminating the need for a user to access the impact surface prior to particle sampling. The invention also provides optically transparent particle impactors capable of in situ optical and/or visual analysis of particles, such as viable biological particles, without the need for physical access or handling of the impact surface during sampling, growth and optical characterization of viable biological particles.

In an aspect, the invention provides an impactor comprising: (i) a sampling head comprising one or more intake apertures for sampling a fluid flow containing biological particles; and (ii) an impactor base operationally connected to receive at least a portion of the fluid flow from the sampling head; the impactor base comprising an impact surface for receiving at least a portion of the biological particles in the fluid flow and an outlet for exhausting the fluid flow; wherein the sampling head and the impactor base are integrated components that engage to enclose the impact surface; and wherein the device provides for sampling of the biological particles and growth of the biological particles received on the impact surface without disengaging the sampling head and the impactor base.

In another aspect, the invention provides an impactor comprising: (i) a sampling head comprising one or more intake apertures for sampling a fluid flow containing particles; and (ii) an impactor base operationally connected to receive at least a portion of the fluid flow from the sampling head; the impactor base comprising an impact surface for receiving at least a portion of the particles in the fluid flow and an outlet for exhausting the fluid flow; wherein the sampling head and the impactor base are integrated components that engage to enclose the impact surface; and wherein the device is capable of being sterilized in a fully assembled configuration wherein the impact surface remains enclosed by the sampling head and impactor base.

Impactor devices of the invention include single-use devices and/or disposable devices. Impactors of the invention are useful for monitoring biological particles in a cleanroom, aseptic or healthcare environment. Impactors of the invention are useful for sampling particles in a range of fluids including air or one or more process gases for a manufacturing application. Impactors of the invention are useful for sampling, growing and analyzing biological particles comprising viable microorganisms.

In an embodiment, for example, the impactor base further comprises a growth medium positioned to receive the particles in the fluid flow, wherein the impact surface is a receiving surface of the growth medium. Useful growth media include culture medium, such as agar, broth, and other substrates, such as filters. In an embodiment, the growth medium is provided in a petri dish comprising an integrated component of the impactor base, for example, wherein the petri dish is cast in a single piece with the impactor base. In an embodiment, for example, the petri dish and impactor base comprise a single unitary element, such as a unitary component comprising a single cast polymer structure. In an embodiment, for example, the growth medium comprises an agar plate. In an embodiment, the sampling head and the impactor base engage, optionally reversibly, to entirely contain the impact surface, for example providing an airtight seal around the impact surface, thus only allowing fluid to pass through the intake apertures and interact with the impact surface.

In an embodiment, for example, the impactor further comprises a selectively removable cover provided on the sampling head for covering the intake apertures, thereby maintaining a sterile environment for the growth medium prior to sampling the fluid flow containing particles or for providing a hermetically sealed environment for the growth medium after sampling the fluid flow containing particles. In an embodiment, for example, the impactor base, sampling head or both are optically transparent so as to allow visualization, optical detection or imaging of particles in the growth medium without physically accessing the growth medium.

In an embodiment, for example, the sampling head and the impactor base each independently comprise a molded or cast structure. In an embodiment, for example, the sampling head provides a substantially laminar flow of the fluid through the impactor base. In an embodiment, for example, the intake apertures of the sampling head comprise a plurality of slits or holes provided in a preselected pattern. In an embodiment, for example, the sampling head and the impactor base engage so as to provide the impact surface at a preselected distance from the intake apertures of the sampling head to allow for collection of at least 50% of the particles having cross sectional dimensions greater than or equal to 0.5 µm. In an embodiment, for example, the sampling head and the impactor base engage via a substantially airtight seal. In an embodiment, for example, the sampling head and the impactor base engage via a selectively removable interlocking connection. In an embodiment, for example, the sampling head and the impactor base engage via an O-ring connection, for example, provided between a bottom surface of the sampling head and a top surface of the impactor base.

Impactors of the invention may comprise a range of useful materials. In an embodiment, for example, the sampling head and the impactor base each independently comprise a polymer material, such as a synthetic or natural polymer. In an embodiment, for example, the sampling head and the impactor base each independently comprise a sterile material.

In an embodiment, for example, the outlet of the impactor base is connected to a fan or pump for providing the fluid flow through the impactor, wherein the flow changes direction after passing through the intake apertures. In an embodiment, for example, the direction of the fluid changes by more than 20 degrees after passage through the intake apertures, and optionally more than 40 degrees after passage through the intake apertures. Implementation of a change in the direction of the fluid flow after passage through the intake apertures is useful for providing high efficiency collection of particles having preselected cross sectional dimensions, e.g., diameter or effective diameter greater than or equal to a threshold value.

The invention includes impactors comprising optically transparent components, for example, to allow for efficient use in a fully assembled configuration. In an embodiment, for example, at least a portion of the impactor base, sampling head or both are optically transparent to allow characterization of the particles on the impact surface without disengaging the sampling head and the impactor base. In an embodiment, for example, the impactor base, sampling head or both are optically transparent so as to provide a transmission greater than or equal to 50% for at least a portion of incident light having a wavelength from the range of 400 nm to 800 nm. In an embodiment, for example, the impactor base, sampling head or both are optically transparent so as to allow visualization, optical detection or imaging of particles on the impact surface without disengaging the sampling head and the impactor base. In an embodiment, for example, the impactor base, sampling head or both are optically transparent so as to allow determination of the amount of viable biological particles on the impact surface. In an embodiment, for example, the impactor base, sampling head or both are optically transparent so as to allow determination of the genus or species of viable biological particles on the impact surface.

The impactors of the present invention may include a range of additional structural features to facilitate effective use and avoidance of contamination. In an embodiment, the impactor base has a plurality of grooves provided on an outer surface to allow for effective handling of the impactor by a user, for example, by providing an exterior surface allowing for a user to easily transfer the device to and from a sampling environment. In an embodiment, the impactor base has one or more recessed features to allow for effective stacking of a plurality of the impactors, thereby minimizing the potential of the stacked impactor to fall and potentially become damaged or contaminated during transfer to and from a sampler.

In another aspect, the invention provides a method for sampling biological particles from a fluid flow comprising the steps of: (i) sampling the fluid flow with an impactor; the sampler comprising: (1) a sampling head comprising one or more intake apertures for sampling the fluid flow containing the biological particles; (2) an impactor base operationally connected to receive at least a portion of the fluid flow from the sampling head; the impactor base comprising an impact surface positioned to receive at least a portion of the biological particles in the fluid flow and an outlet for exhausting the fluid flow, wherein the sampling head and the impactor base are integrated components that engage to enclose the impact surface; and (ii) growing at least a portion of the biological particles received by the impact surface; wherein the growing step is carried out without disengaging the sampling head and the impactor base. Methods of this aspect may include growth of viable biological particles, for example, via reproduction in a growth medium, such as a culture. The invention includes particle sampling, collection and detection methods as carried out with any of the devices as set forth herein.

In another aspect, the invention provides a method for sampling biological particles from a fluid flow, the method comprising the steps of: (i) providing an impactor comprising: (1) a sampling head comprising one or more intake apertures for sampling a fluid flow containing particles; and (2) an impactor base operationally connected to receive at least a portion of the fluid flow from the sampling head; the impactor base comprising an impact surface for receiving at least a portion of the particles in the fluid flow and an outlet for exhausting the fluid flow; wherein the sampling head and the impactor base are integrated components that engage to enclose the impact surface; (ii) sterilizing the impactor in a fully assembled configuration wherein the impact surface remains enclosed by the sampling head and impactor base during sterilization; (iii) sampling the fluid flow with the impactor, wherein particles in the fluid are received by the impactor surface; and growing at least a portion of the biological particles received by the impact surface; wherein the growing step is carried out without disengaging the sampling head and the impactor base.

A method of the invention further comprises the step of detecting viable biological particles received by the impact surface. In an embodiment, for example, at least a portion of the impactor base, sampling head or both are optically transparent, the method further comprising optically characterizing at least a portion of the particles without disengaging the sampling head and the impactor base, for example wherein optically characterizing is achieved by visualizing, optically detecting or imaging the particles. In an embodiment, for example, the impactor base further comprises a growth medium positioned to receive the particles in the fluid flow, wherein the impact surface is a receiving surface of the growth medium. In an embodiment, for example, the growing step comprises allowing the biological particles comprising microorganisms to grow until visible by eye or detectable using an optical detector or imaging device.

In some embodiments, methods and devices of the invention provide a benefit of minimizing, or entirely eliminating, the need for a user to physically access the impact surface after sterilization. In an embodiment, for example, the method does not include a user physically contacting the growth medium after being contacted with the particles. In an embodiment, for example, a method of the invention further comprises the step of providing a cover on the sampling head for covering the intake apertures, thereby sealing the growth medium within the device after the sampling step.

In an embodiment, for example, the invention provides a method of sampling the fluid containing the particles using the impactor for a single use only, and optionally disposing of the impactor after use. In an embodiment, for example, the invention provides a method of monitoring biological particles in cleanroom or aseptic environments. In an embodiment, for example, the invention provides a method of monitoring biological particles in air or one or more process gases. In an embodiment, for example, a method of the invention further comprises repeating the steps of the method using a new sampler.

In an aspect, the invention provides a method of making an impactor comprising the steps of: (i) providing a sampling head comprising one or more intake apertures for sampling a fluid flow containing biological particles; (ii) providing an impactor base operationally connected to receive at least a portion of the fluid flow from the sampling head; the impactor base comprising an impact surface for receiving at least a portion of the biological particles in the fluid flow and an outlet for exhausting the fluid flow; and (iii) sterilizing the impactor in a fully assembled configuration wherein the impact surface remains enclosed by the sampling head and impactor base.

In an aspect, the invention provides a method of making an impactor comprising the steps of: (i) molding a sampling head comprising one or more intake apertures independently having lateral and thickness dimensions; (ii) molding an impactor base comprising a growth medium reservoir and an outlet, wherein the sampling head and impactor base are designed to engage to enclose the growth medium reservoir; and (ii) optically inspecting the molded sample head to verify at least one physical dimension of the intake apertures is within one or more preselected tolerance ranges. In an embodiment, for example, the intake apertures are slits and the step of optically inspecting comprises verifying at least one lateral dimension of each of the intake apertures is independently within one or more preselected tolerance ranges. In an embodiment, for example, inspecting comprises optically verifying at least three opening dimensions of each slit. In an embodiment, for example, the step of optically inspecting the molded sample head is carried out using an automated high-speed camera to image the intake apertures of the sampling head.

Some methods of the invention further comprise providing an O-ring on the sampling head or the impactor base to allow for forming a seal between the sampling head and the impactor base. Some methods of the invention further comprise inspecting the molded impactor base via a batch sampling inspection. Some methods of the invention further comprise providing the growth medium to the growth medium reservoir, and subsequently engaging the sampling head and the impactor base so as to enclose the growth medium reservoir having the growth medium. Some methods of the invention further comprise sterilizing the sample head and impactor base.

The devices and methods of the present invention are versatile and support a range of particle sampling, monitoring and analysis applications. For example, the present devices and methods are useful for applications involving preparation, handling, manufacture, storage, transfer, fill and/or finish of sterile pharmaceutical or biological agents, pharmaceutical or biological containers, pharmaceutical or biological delivery devices, medical devices including implantable devices, blood, cell and tissue materials. In addition, the present devices and methods are useful for monitoring and characterizing biological particles in healthcare environments, such as hospitals, operating rooms, surgical suites and compounding pharmacies. Other applications of the present devices and methods include the preparation, manufacture, storage, transfer or processing of cosmetics, personal care products, food and beverages.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 12 provides a flow diagram illustrating a method for sampling biological particles from a fluid flow.

DETAILED DESCRIPTION OF THE INVENTION

Figure 1A:
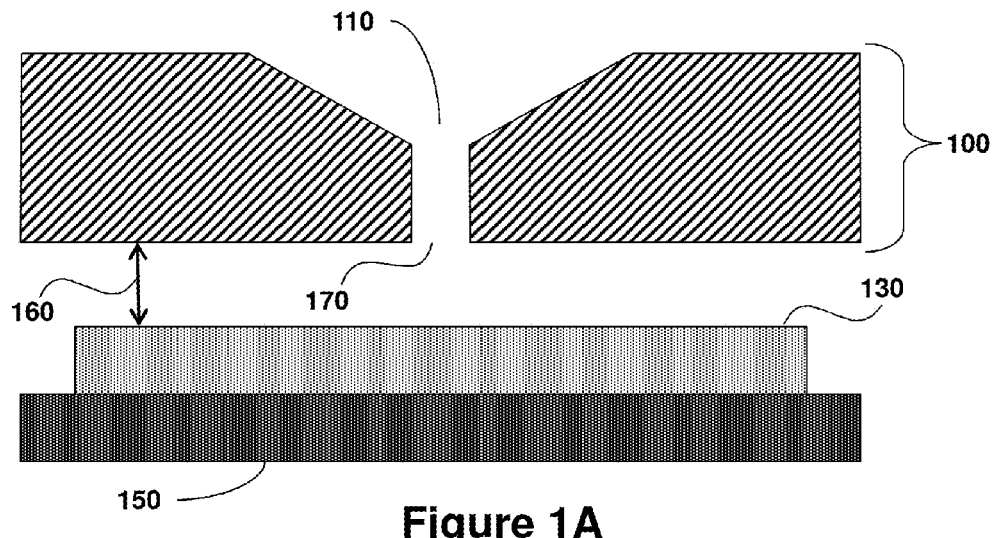
FIG. 1A provides a schematic diagram illustrating the general construction of a particle impactor and FIG. 1B illustrates an expanded view of a particle impactor to further illustrate the operational principal.

In general, the terms and phrases used herein have their art-recognized meaning, which can be found by reference to standard texts, journal references and contexts known to those skilled in the art. The following definitions are provided to clarify their specific use in the context of the invention.

"Particle" refers to a small object which is often regarded as a contaminant. A particle can be any material created by the act of friction, for example when two surfaces come into mechanical contact and there is mechanical movement. Particles can be composed of aggregates of material, such as dust, dirt, smoke, ash, water, soot, metal, minerals, or any combination of these or other materials or contaminants. "Particles" may also refer to biological particles, for example, viruses, spores and microorganisms including bacteria, fungi, archaea, protists, other single cell microorganisms. Biological particles include, but are not limited to, microorganisms having a size on the order of 0.1-20 µm. Biological particles include viable biological particles capable of reproduction, for example, upon incubation within a growth media. A particle may refer to any small object which absorbs or scatters light and is thus detectable by an optical particle counter. As used herein, "particle" is intended to be exclusive of the individual atoms or molecules of a carrier fluid, for example, such gases present in air (e.g., oxygen molecules, nitrogen molecules, argon molecule, etc.) or process gases. Some embodiments of the present invention are capable of sampling, collecting, detecting, sizing, and/or counting particles comprising aggregates of material having a size greater than 50 nm, 100 nm, 1 µm or greater, or 10 µm or greater. Specific particles include particles having a size selected from 50 nm to 50 µm, a size selected from 100 nm to 10 µm, or a size selected from 500 nm to 5 µm.

The expression "sampling a particle" broadly refers to collection of particles in a fluid flow, for example, from an environment undergoing monitoring. Sampling in this context includes transfer of particles in a fluid flow to an impact surface, for example, the receiving surface of a growth medium. Alternatively sampling may refer to passing particles in a fluid through a particle analysis region, for example, for optical detection and/or characterization. Sampling may refer to collection of particles having one or more preselected characteristics, such as size (e.g., cross sectional dimension such as diameter, effective diameter, etc.), particle type (biological or nonbiological, viable or nonviable, etc.) or particle composition. Sampling may optionally include analysis of collected particles, for example, via subsequent optical analysis, imaging analysis or visual analysis. Sampling may optionally include growth of viable biological particles, for sample, via an incubation process involving a growth medium. A sampler refers to a device for sampling particles.

"Impactor" refers to a device for sampling particles. In some embodiments, an impactor comprises a sample head including one or more'intake apertures for sampling a fluid flow containing particles, whereby at least a portion of the particles are directed onto an impact surface for collection, such as the receiving surface of a growth medium (e.g., culture medium such as agar, broth, etc.) or a substrate such as a filter. Impactors of some embodiments, provide a change of direction of the flow after passage through the intake apertures, wherein particles having preselected characteristics (e.g., size greater than a threshold value) do not make the change in direction and, thus, are received by the impact surface.

The expression "detecting a particle" broadly refers to sensing, identifying the presence of and/or characterizing a particle. In some embodiments, detecting a particle refers to counting particles. In some embodiments, detecting a particle refers to characterizing and/or measuring a physical characteristic of a particle, such as diameter, cross sectional dimension, shape, size, aerodynamic size, or any combination of these. A particle counter is a device for counting the number of particles in a fluid or volume of fluid, and optionally may also provide for characterization of the particles, for example, on the basis of size (e.g., cross sectional dimension such as diameter or effective diameter), particle type (e.g. biological or nonbiological), or particle composition. An optical particle counter is a device that detects particles by measuring scattering, emission or absorbance of light by particles.

"Flow direction" refers to an axis parallel to the direction the bulk of a fluid is moving when a fluid is flowing. For fluid flowing through a straight flow cell, the flow direction is parallel to the path the bulk of the fluid takes. For fluid flowing through a curved flow cell, the flow direction may be considered tangential to the path the bulk of the fluid takes.

"Optical communication" refers to an orientation of components such that the components are arranged in a manner that allows light or electromagnetic radiation to transfer between the components.

"Fluid communication" refers to the arrangement of two or more objects such that a fluid can be transported to, past, through or from one object to another. For example, in some embodiments two objects are in fluid communication with one another if a fluid flow path is provided directly between the two objects. In some embodiments, two objects are in fluid communication with one another if a fluid flow path is provided indirectly between the two objects, such as by including one or more other objects or flow paths between the two objects. For example, in one embodiment, the following components of a particle impactor are in fluid communication with one another: one or more intake apertures, an impact surface, a fluid outlet, a flow restriction, a pressure sensor, a flow generating device. In one embodiment, two objects present in a body of fluid are not necessarily in fluid communication with one another unless fluid from the first object is drawn to, past and/or through the second object, such as along a flow path.

"Flow rate" refers to an amount of fluid flowing past a specified point or through a specified area, such as through intake apertures or a fluid outlet of a particle impactor. In one embodiment a flow rate refers to a mass flow rate, i.e., a mass of the fluid flowing past a specified point or through a specified area. In one embodiment, a flow rate is a volumetric flow rate, i.e., a volume of the fluid flowing past a specified point or through a specified area.

"Pressure" refers to a measure of a force exhibited per unit area. In an embodiment, a pressure refers to a force exhibited by a gas or fluid per unit area. An "absolute pressure" refers to a measure of the pressure exerted by a gas or fluid per unit area as referenced against a perfect vacuum or volume exerting zero force per unit area. Absolute pressure is distinguished from a "differential pressure" or "gauge pressure", which refers to a relative change or difference in force exhibited per unit area in excess of or relative to a second pressure, such as an ambient pressure or atmospheric pressure.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

Figure 1B:
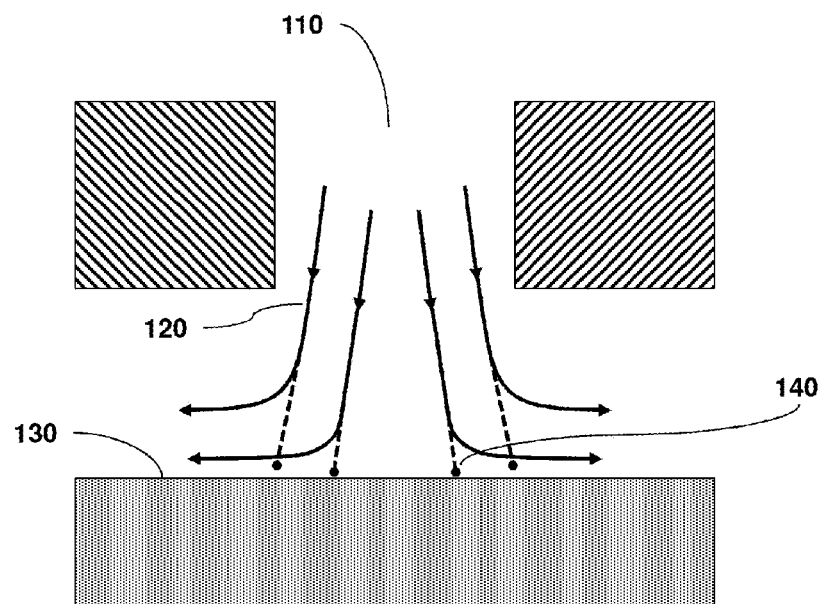

FIG. 1A provides a schematic diagram illustrating the general construction of a particle impactor and FIG. 1B illustrates an expanded view of a particle impactor to further illustrate the operational principal. As shown in these Figures, gas flow is directed through an intake aperture 110 in a sampling head 100 where it is accelerated towards an impact surface 130, which forces the gas to rapidly change direction, following flow paths 120. Due to their momentum, particles 140 entrained in the gas flow are unable to make the rapid change in direction and impact on the impact surface 130. In the embodiment shown in FIGS. 1A and 1B, impact surface 130 is supported by impactor base 150. In embodiments, impact surface 130 comprises the receiving surface of a growth medium, such as agar, provided in a growth medium container or petri dish. Viable biological particles collected on the impact surface, for example, can subsequently be grown and evaluated to provide an analysis of the composition of the fluid flow sampled. For collection of biological particles on the impact surface, control over the distance 160 between the exit 170 of the intake aperture 110 and the impact surface is important. If the distance 160 is too large, for example, the particles may sufficiently follow the fluid path so as to avoid impact with the impact surface. If the distance 160 is too small, however, the particles may impact the impact surface with a force sufficient to render the particles non-viable, and therefore unable to reproduce.

The invention provides air samplers, including impactors, for analysis of viable biological particles in an environment undergoing monitoring, such as an aseptic manufacturing environment. An aspect of the invention is an impactor device that integrates an agar media plate with an air sampler in an integrated single-use and/or disposable package. The present impactors are well adapted for use in cleanroom environments, particularly aseptic environments, where medical products are manufactured, such as sterile medicinal products (e.g., pharmaceuticals, biologicals, diagnostics, medical devices, medical implants, etc.). In an embodiment, for example, a connector on the side of the device supports connection of a vacuum source (e.g., portable vacuum source (e.g., pump or fan) or house vacuum line) that draws air into slit-shaped air inlets (e.g., 20 slits, 0.1 mm nominal width) where particles are subsequently impacted onto the receiving surface of a growth medium, such as agar media. After the cleanroom air is sampled, the device is transferred to a lab for incubation for multiple days to promote growth of viable microorganisms sampled. Lab technicians then count the number of CFU (colony forming units) and, if present, identify the genus or species of the microorganisms present.

Impactors of the invention provide a number of technical benefits including the following.

Elimination of False-Positive Contamination

With the conventional methods of microbial air sampling, the operators load an agar plate into a stainless steel sampling head device. In this process, the operators must directly contact the plate to load and unload the agar plate. When this process is carried out carefully and properly, the operator should not contaminate the media. However, it does routinely happen that the operator may contaminate the plate, creating a "false positive" (i.e. growth of microorganisms that did not come from the environment during the production batch, but from the handling by the operator before or after the production batch). When positive microbial growth is observed, the manufacturer's quality department must conduct an investigation to determine the level of risk to the finished drug product and decide whether to discard the batch or continue and ship the product. These investigations must be very thorough and are very costly (e.g., a quality investigation like this can cost the company anywhere from $5K to $18K per investigation). If the batch is discarded, it can result in losses of thousands to millions of dollars, depending on the market value of the product and the material and production costs of the product. In addition, false positives can also put the final patient at risk. In any investigation, human error can occur. Sometimes the quality department of a manufacturer may decide that a contamination event was a false positive, whereas actually it was real contamination that may compromise the purity of the drug product and put consumers/patients at risk of illness, injury or death.

The device of the present invention reduces, or essentially eliminates, the possibility of false-positive contaminants from operator handling. The media plate in the present single-use impactor device remains protected inside the device during sterilization, sampling, incubation and analysis processes—as it does not have to be loaded and unloaded into a sampler since it always remains inside the sampler. The operator contacts and handles the outside device itself, and in contrast the media plate is not directly handled or physically contacted by the user.

Also, when an operator loads/unloads a normal agar plate in a traditional sampler, the media is fully exposed to the air temporarily before or after sampling takes place (e.g., when the drug is not being produced). False positives may occur during this time. In the traditional application, "fully exposed" means the entire 90 mm diameter of the media (6362 $mm^2$ surface area) is exposed. This is contrasted against the negligible exposure of the media in the present single-use device—the only exposure is the 20 slits that are 0.1 mm wide.

Finally, the results of sampling using the present impactors can be analyzed in the lab without ever opening the device (other than removing and replacing the top lid during the sampling period—but the plate itself can remain enclosed inside). In an embodiment, for example, the plastic material is optically transparent, and any CFU microorganism growth can be seen and counted from beneath the plate without removing the top portion of the head. If there is CFU growth and the technician must identify the type, then the top portion has to be removed to access the agar media for staining or other identification techniques. But the majority of the time, however, the result in the most critical aseptic areas is zero or one CFU (within tolerance not requiring identification).

Elimination of Sterilization Costs and Risks

In traditional air sampling applications, the agar plate is loaded in a stainless steel sampling device intended for reuse. That stainless steel sampler must be disinfected (sprayed with disinfecting chemicals and wiped down) and transferred to an autoclave for sterilization (an autoclave is a high-pressure, high-temperature steam sterilizing chamber) for it to be reused effectively without significant risk of contamination. There are numerous costs to these activities involved in reuse including the costs of disinfectants, wipes, autoclave power and utilities, and significant labor hours and lost productivity time. All of these disinfecting and sterilizing activities are eliminated with a single-use device approach. In addition, the transfer of the stainless steel sampler back to the production floor (from the autoclave) introduces cross-contamination and handling risks. The sampler can be re-contaminated after it is sterilized due to the handling and transfer activities and logistics back to the cleanroom (another potential source of false positives).

These risks and costs are all eliminated with the present invention that supports an efficient single-use approach to sampling biological particles.

Improved Ergonomics, Occupational Health and Safety

Stainless steel is a dense, heavy material and stainless steel samplers often require twisting, and at least lifting and moving, while traditional agar plates are loaded and unloaded in the device. The stainless steel sampling heads are light enough to handle with one hand, but the repetitive action creates risk of occupational injury—not to mention the risk of dropping stainless steel on one's foot or other body part, which can happen when loading/unloading plates, or on the transfer of the steel head to/from the autoclave. The occupational movements with the stainless steel heads are especially difficult inside aseptic production equipment, which are often protected from human intervention and can only be accessed through glove ports in walls (isolator glove boxes and the like).

The single-use sampling device of some aspects of the invention is plastic and very light weight—much lighter than a stainless steel head. And the lid never has to be removed, which cuts down on repetitive occupational motion by operators. During use, for example, a single-use sampling device of the invention can simply be 'plugged' and 'unplugged' into a vacuum port with the loading and unloading activity.

The design of the single-use device incorporates "grooves" in the bottom/base portion of the sampler to allow an easier grip by the operator when loading and unloading the sampler. The grooves are spaced in such a way to accommodate a variety of hand sizes/finger spacing.

Stable and Safe Transfer of Samples from the Cleanroom to the Lab

With traditional agar media plates, when the sampling is finished, a lid is placed over the plate and often the plates are stacked on a cart and taken from the cleanroom to the lab. Sometimes the stack of plates can fall over or fall off the cart as the cart moves around and experiences vibration, wheel-wobble, hitting other objects, etc. If the plates fall over or fall off the cart after sampling, the samples are compromised and the results are then questionable. This is another potential source of false positives, with all the same negative consequences for the manufacturer (and potentially for the patient) that were described above.

With the single-use impactor device of the invention, the bottom/base of the unit has a circular 'indentation' underneath the device. This indentation is in the same diameter as the lid that goes on top. Therefore when the plates are stacked, there is some "interlocking" between the devices above and below each other. This does not eliminate the possibility of the devices falling over or falling off the cart, but it decreases the possibility significantly.

High Physical and Biological Collection Efficiency

An important element to the performance of a microbiological air sampler is to have high physical and biological collection efficiency in the target range of particle sizes. Physical collection efficiency is the percentage of particles that are physically collected (impacted) onto the media at a certain particle size. Biological collection efficiency is the percentage of viable biological particles that not only impact onto the media, but that also grow so that they can be counted and identified. As air enters the inlets of the sampling device, each inlet acts as a nozzle to accelerate the particles onto the media.

The velocity of the particles (driven mostly by flow rate of the air through the device and the size and shape of the inlet opening) entering the chamber is one key factor to the collection efficiency. But another key factor is the inlet-to-agar surface distance (e.g., when using slits as inlets and an agar media, this parameter may be referred to as the slit-to-agar distance). The slit-to-agar distance is important to collection efficiency because if this distance is too far, desired particles may navigate the turn and avoid being impacted onto the media and will be exhausted through the vacuum port. If the distance is too short, the physical collection efficiency will improve, but the biological efficiency may suffer as the velocity of the particles may be too high. Therefore there is an ideal slit-to-agar distance for any microbial air sampler design, and this slit-to-agar distance is not only driven by the dimensions and design of the air sampler, but also based on the dimensions, design, and agar fill volume of the agar media plate placed inside of the sampler.

With conventional sampling approaches where an agar media plate is placed inside a stainless steel sampler, there can be a very wide range of distance from the inlet to the media surface. The media plates are often made by a different company than the sampler and the stainless steel samplers are designed typically to accommodate a wide range of media plate dimensions and types (as one might expect, to maximize the use of the sampler itself). This typically results in the distance from the inlet to the agar surface being further than it ideally should be, which results in target particles being missed.

With the present single-use sampling device, the slit-to-agar distance is preset at a value providing high physical and biological collection efficiencies. Since the media plate is built into the actual device, the slit-to-agar distance does not change unless the agar volume changes (which is controlled in the filling process). This not only assures high collection efficiency performance of the design, but also reduces sample-to-sample variance.

EXAMPLE 1

Device For Microbial Air Sampling

Description

In an embodiment, the invention relates to a disposable device for microbial air sampling. The control of microbial contamination in environments wherein aseptic working conditions are required is extremely important, but not the sole aspect in the preparation of products such as drugs.

Several methods and devices are known for the control and/or quantification of contamination of air by microorganisms. These include impact devices or "impactors" principally consisting of a containment head within which is housed a Petri dish. Specifically, the principle on which the impactors are based is that the air to be analyzed is forced, by means of a suction pump, for example, in order to penetrate into the sampling head where, due to the impact with the culture medium of the Petri dish, the deposition of particles in the air on the same medium is guaranteed. In some devices, the Petri dish is placed inside the impactor whenever it is necessary to perform a check on air contamination, and the same is removed at the end of each sampling and incubated under conditions suitable for the growth of the microorganisms that might be deposited. After incubation, counting the number of visible colonies provides an estimate of the contamination, in terms of colony-forming units (CFU), of the air sample analyzed.

Such devices, although very useful, have some disadvantages. In fact, among the disadvantages is the need to insert and remove the Petri dish from the impactor whenever one must analyze air pollution, with the resulting increase in the risk of contamination of the culture medium present therein. In fact, the operator is forced during each analysis to manipulate the device, a process involving at least the steps of: opening of the sampling head, insertion of the plate, exposure of the culture medium to air by removal of the protective cover and closure of the sampling head. In addition, at the end of the sampling, it is necessary to carry out similar operations to remove the Petri dish from the impactor. Specifically, these operations consist of: opening of the sampling head by the operator, removal of the dish, protection of the medium on which the particles deposited are present by, for example, closure of the Petri dish with a lid for protection and transport in an incubator.

It follows, therefore, that the use of devices for air sampling of the type described above requiring continuous intervention by the operator have a greater risk of contamination of the culture medium, which ultimately translates into an increase in false positives with consequent alterations of the actual estimate of contamination of the air sample under analysis.

The impactors presently on the market have a number of disadvantages, which include those mentioned above that actually limit their reliability. A purpose of the present invention is to provide a new and original solution for addressing the substantial disadvantages present in the state of the prior art.

This disclosure relates to a device for microbial air sampling characterized in that it is shaped in such a way as to allow for sampling while minimizing manipulation by the operator. In other words, the invention described herein permits safe handling in terms of contamination, since it is no longer necessary that the operator take actions such as for example: opening the impactor head, positioning the Petri dish in the base of the impactor, removing the lid of the Petri dish and closing the impactor head.

An advantage of the device described herein is the ability to control contamination, for example in sterile environments, effectively as compared to known devices. In fact, the reduced manipulation by the operator of the device itself actually reduces the risk of false positives observed during the analysis of the air sample. Moreover, as certain devices of the invention are disposable, the problems relating to the cleaning of known impactors are eliminated. This aspect of the invention provides additional safety in the result of the analysis carried out from the time that the entire device is replaced with each new sampling, thereby reducing any interference between samples taken at different times.

Additional advantages, as well as the features and modes of operation of this invention, will become apparent from the following detailed description of its possible embodiments, presented by way of example and not of limitation, by making reference to the figures of the accompanying drawings, which present specific embodiments of the invention.

Figure 2:
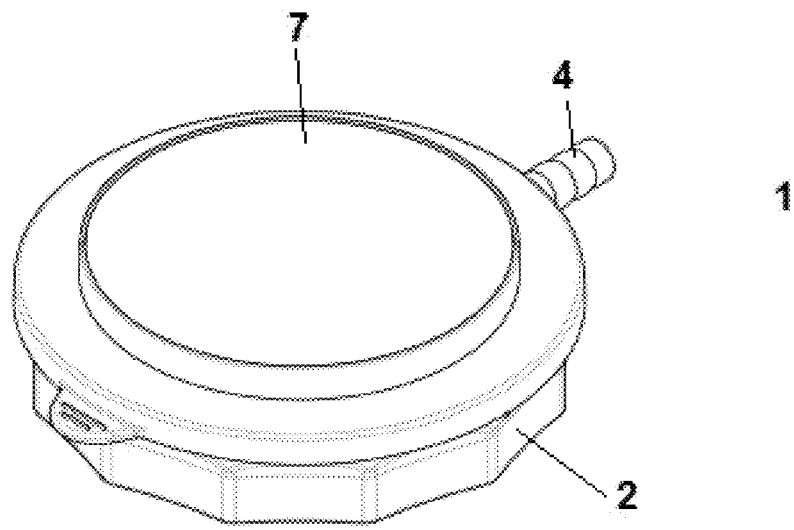
FIG. 2 shows a perspective view of an impactor of the present invention.

FIG. 2 shows a perspective view of an impactor of the present invention

Figure 3:
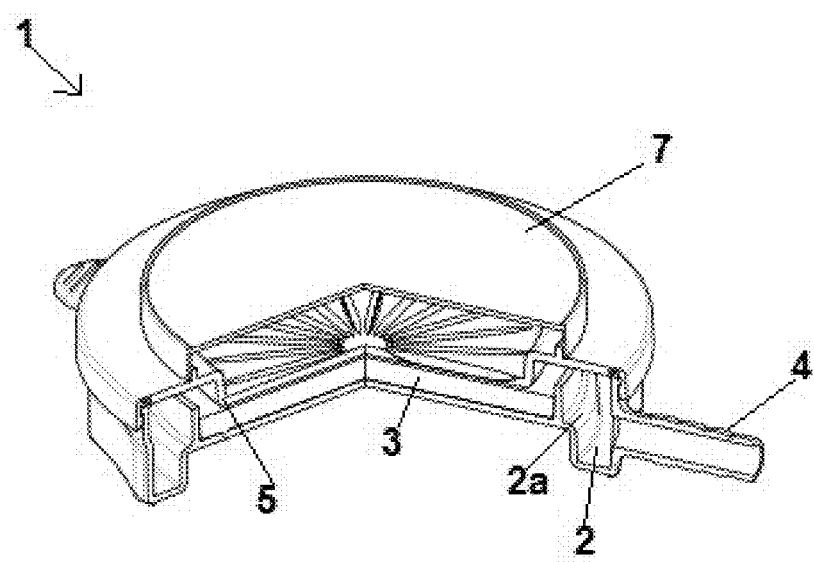
FIG. 3 shows a sectional view of the impactor of FIG. 2.

FIG. 3 shows a sectional view of the impactor of FIG. 2.

Figure 4:
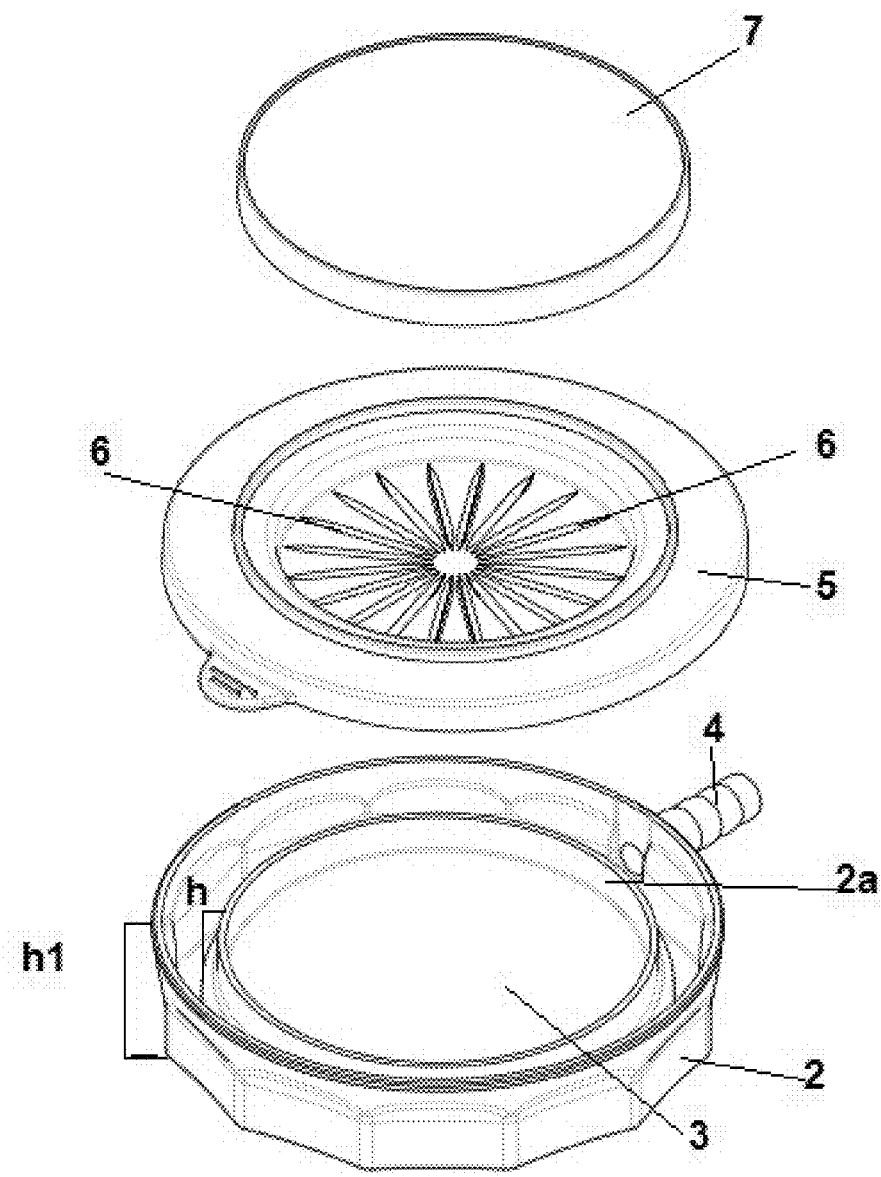
FIG. 4 is an exploded view of an impactor of the present invention wherein components of the device are spatially separated for clarity.

FIG. 4 is an exploded view of an impactor of the present invention wherein components of the device are spatially separated for clarity.

Figure 5:
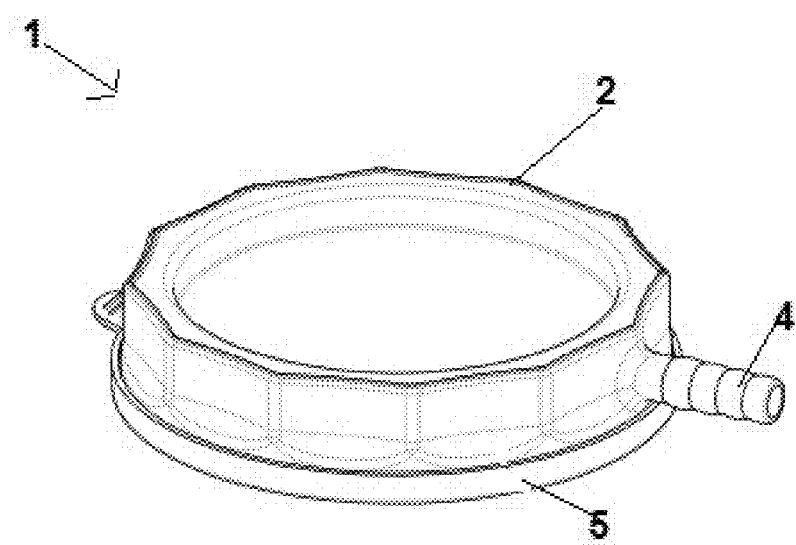
FIG. 5 shows a perspective view of an impactor of the present invention.

FIG. 5 shows a perspective view of an impactor of the present invention.

With reference to FIGS. 2 to 5, a device for microbial air sampling according to an embodiment of the invention is generally denoted by 1.

Device 1 comprises a base portion 2, a dispensing portion 5 and a protective portion 7. Furthermore, device 1 as a whole is disposable or usable for a single sampling of the air to be analyzed. In particular, base portion 2 comprises a support 2A suitable for accommodating a culture medium 3 for the growth of microorganisms. Preferably, said support 2A may be a Petri dish. In a preferred embodiment of the present invention, the support 2A has a height h and an area A smaller than the height h1 and the area A1 of the base portion 2.

Purely by way of example and not limitation, the height h of said support 2A has a value of between 17 mm and 19 mm, and the area A of said support 2A has a value of between 5,930 mm$^2$ and 5,940 mm$^2$. Furthermore, the height h1 of the base portion 2 may have a value of between 22 mm and 24 mm, and the area A1 of the base portion 2 may have a value of between 10,730 mm$^2$ and 10,760 mm$^2$.

As indicated above, support 2A is adapted to receive a culture medium 3 suitable for growth of microorganisms, for example, when device 1 is placed in conditions of temperature and $O_2/CO_2$ favorable to the growth of colony-forming units (CFU). Depending on the type of microorganism whose presence in the air of the environment is to be analyzed, the technician of the sector using his/her basic knowledge will be able to identify, among the known culture media, the one most suitable to his/her needs. Purely by way of example and not limitation, culture medium 3 can be chosen from TSA (Tryptone Soy Agar) or SDA (Sabouraud Dextrose Agar). For the purposes of the present invention, the amount of culture medium 3 present in the support 2A is such as to ensure the growth of microbial colonies on said medium. In this perspective, the support 2A is preferably adapted to receive a volume of 20-40 ml of medium.

Base portion 2 includes, as evident from FIGS. 2-5, a conduit 4 for a fluid, adapted to connect an interior region of said base portion 2 with the outside. Preferably, said conduit is closed, for example by means of a cap placed on its free end, when the device is not performing air sampling, such as during transport of device 1 or during its storage. Conversely, when the device is performing air sampling, said conduit is adapted to be connected to a vacuum source in such a way as to facilitate the deposition of microorganisms present in the air sample on culture medium 3, as detailed below.

The dispensing portion 5 of device 1 comprises one or more openings 6 to ensure the passage of airborne microorganisms onto said culture medium 3. To this end, as shown in FIGS. 3 and 4, said one or more openings 6 are positioned adjacent to the culture medium 3 when the dispensing portion 5 is connected to the base portion 2. Said one or more openings 6 may have any type of shape deemed suitable to a person skilled in the art for the purposes of the present invention. Preferably, openings 6 are rectangular in shape and distributed over the entire area (A) of said support 2A. In one embodiment, said one or more openings 6 are distributed in a substantially uniform manner over the entire area A of the support 2A. As shown by way of example in FIGS. 2-5, this uniform distribution can be, for example, a radial pattern. A uniform arrangement of the openings 6 onto the culture medium is particularly advantageous since it allows the identification of the presence of possible false positives during the evaluation phase of the air sample contamination, e.g., where a microorganism is not uniformly distributed and detected across the culture medium.

As indicated above, device 1 operates in a similar manner to impactors for microbial air sampling. Therefore, it is shaped in such a way as to define a connection path of the fluid, namely air, between said one or more openings 6 and said conduit 4.

In order to ensure that the passage of microorganisms preferably takes place only through the openings 6, the dispensing portion 5 and the base portion 2 may be connected to each other to seal, for example, without limitation, by means of an interlocking mechanism.

Device 1 also includes a protective portion 7 that may be positioned on the dispensing portion 5 so as to occlude said one or more openings 6, for example when the device is not performing the air sampling.

In one embodiment of the present invention, the protective portion 7, the base portion 2 and/or the dispensing portion 5 can be made of transparent material. Preferably, the transparent material can be plastic and/or glass. The embodiment of the device 1 in which the dispensing portion 5, the protective portion 7 and/or the base 2 are made of transparent material is particularly advantageous. In fact, once device 1 is placed in temperature, $O_2$ or $CO_2$ conditions suitable to the growth of microorganisms, the count of the colony-forming units (CFU) may be conducted without the need to remove the dispensing portion 5, the protective portion 7 and/or the base 2 in order to access and inspect the culture medium 3. Counting of colony-forming units present in the culture medium 3 provides a quantitative estimate of the contamination of the air sample and then of the air of the environment of interest.

With respect to the mode of operation of device 1, it operates by favoring the deposition of microorganisms present in the air sampled by impact of the air passing into the openings 6 of the culture medium 3.

It is to be understood that there may be other embodiments that belong to the same inventive kernel, all falling within the protective scope of the claims reported herein. Specific embodiments of the invention are further described and set forth below.

In an aspect, the invention provides a device (1) for microbial air sampling comprising a base portion (2) comprising a support (2A) adapted to accommodate a culture medium (3) for the growth of microorganisms; the base portion (2) comprising a conduit (4) for a fluid adapted to connect an inner region of the base portion (2) with the outside; a dispensing portion (5) comprising one or more openings (6) positioned adjacent to the culture medium (3), when connected to the base portion (2), and designed to ensure the passage of microorganisms present in the air onto the culture medium (3); a protective portion (7) positionable on the dispensing portion (5) in such a way as to occlude the one or more openings (6); wherein the device (1) is shaped in such a way as to define a path of fluid connection between the one or more openings (6) and the conduit (4); the device (1) being disposable.

In embodiment, for example, the support (2A) has a height (h) and an area (A) lower than the height (h1) and the area (A1) of the base portion (2). In embodiment, for example, the height (h) of the support (2A) has a value between 17 mm and 19 mm, and the area (A) of the support (2A) has a value between 5,930 $mm^2$ and 5,940 $mm^2$. In embodiment, for example, the height (h1) of the base portion (2) has a value between 22 mm and 24 mm and the area (A1) of the base portion (2) has a value between 10,730 $mm^2$ and 10,760 $mm^2$. In embodiment, for example, the support (2A) is adapted to accommodate a volume of 20-40 ml of culture medium. In embodiment, for example, the one or more openings (6) are distributed in a substantially uniform manner over the entire area (A) of the support (2A), the one or more openings (6) being preferably rectangular in shape. In embodiment, for example, the dispensing portion (5) and the base portion (2) are mutually connected hermetically, preferably by interlocking. In embodiment, for example, the protective portion (7), the base portion (2) and/or the dispensing portion (5) are of transparent material. In embodiment, for example, the transparent material is plastic and/or glass. In embodiment, for example, the side duct (4) is adapted to be connected to a vacuum source in such a way as to facilitate the deposition of microorganisms present in the air sample on the culture medium (3).

EXAMPLE 2

Single-Use Impactor Manufacturing Process

Figure 6:
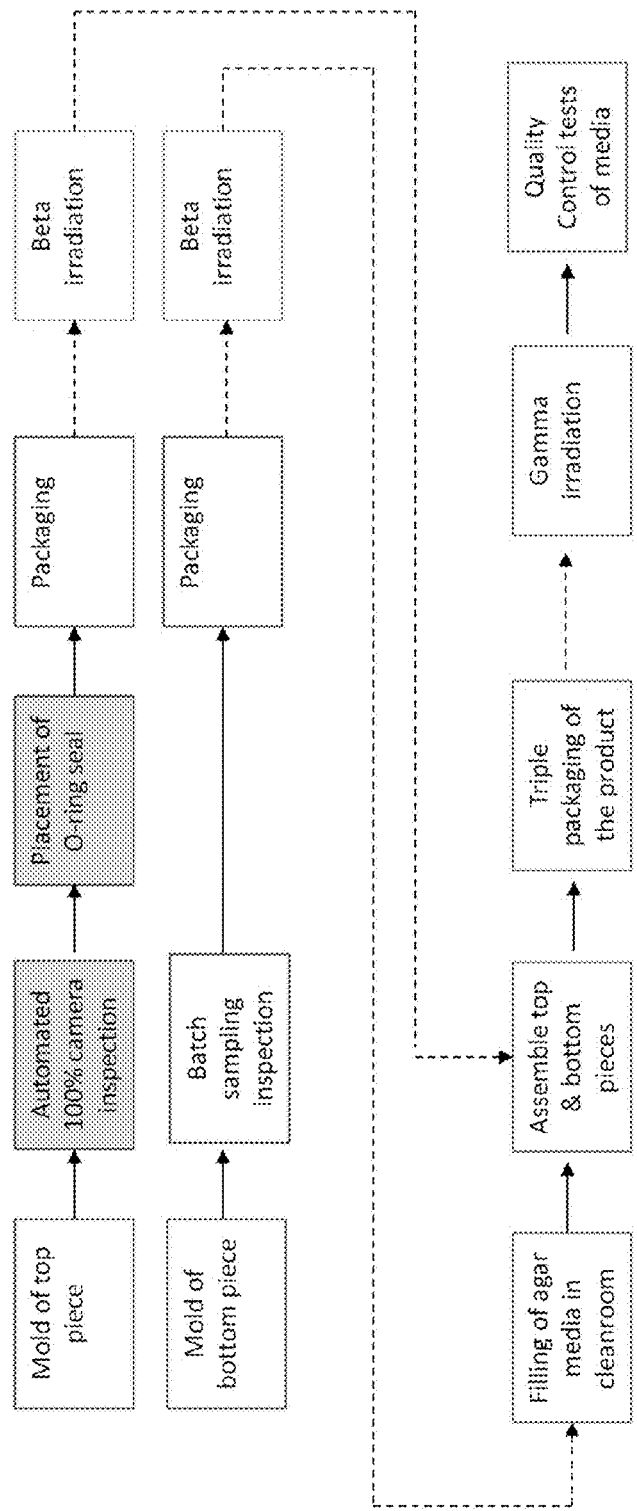
FIG. 6 provides a workflow diagram illustrating a method of making an impactor of the present invention.

FIG. 6 provides a workflow diagram illustrating a method of making an impactor of the present invention. As shown in FIG. 6, the top pieces (e.g., sampling heads) are fabricated using a molding process, optically inspected using a camera for imaging and subsequently an O-ring seal is provided. As shown in FIG. 6, the bottom pieces (e.g., impactor bases) are fabricated using a molding process and inspected via batch sampling. After top and bottom pieces are manufactured, they are each sterilized via exposure to beta radiation. Next, a growth medium, such as agar, is provided to a growth medium container within the impactor base, and top and bottom pieces are subsequently assembled by engaging the O-ring seal between top and bottom pieces. The product is then packaged and sterilized via an additional beta irradiation process. The manufacture process may optionally further include quality control tests, e.g., batch sampling, of the growth media, to ensure sterilization conditions. Certain aspects of the present methods supplement convention manufacture of agar plates including, but not limited to, inspection of the molded top piece via optical inspection, placement of the O-ring, and irradiation of the impactor in a fully assembled configuration.

EXAMPLE 3

Impactor Devices For Sampling Biological Particles

FIGS. 7-11 provide additional schematic drawings illustrating exemplary impactor devices for sampling biological particles. These figures provide exemplary physical dimensions (millimeters), geometries and relative orientations of device components that are useful for certain applications. The specific parameters shown in FIGS. 7-11 are purely exemplary in nature and are not intended to limit the scope of the devices and methods disclosed herein. Devices of the invention are inclusive of a wide range of other physical dimension, geometries, orientations and other variations, as will be readily understood by one having skill in the art.

Figure 7:
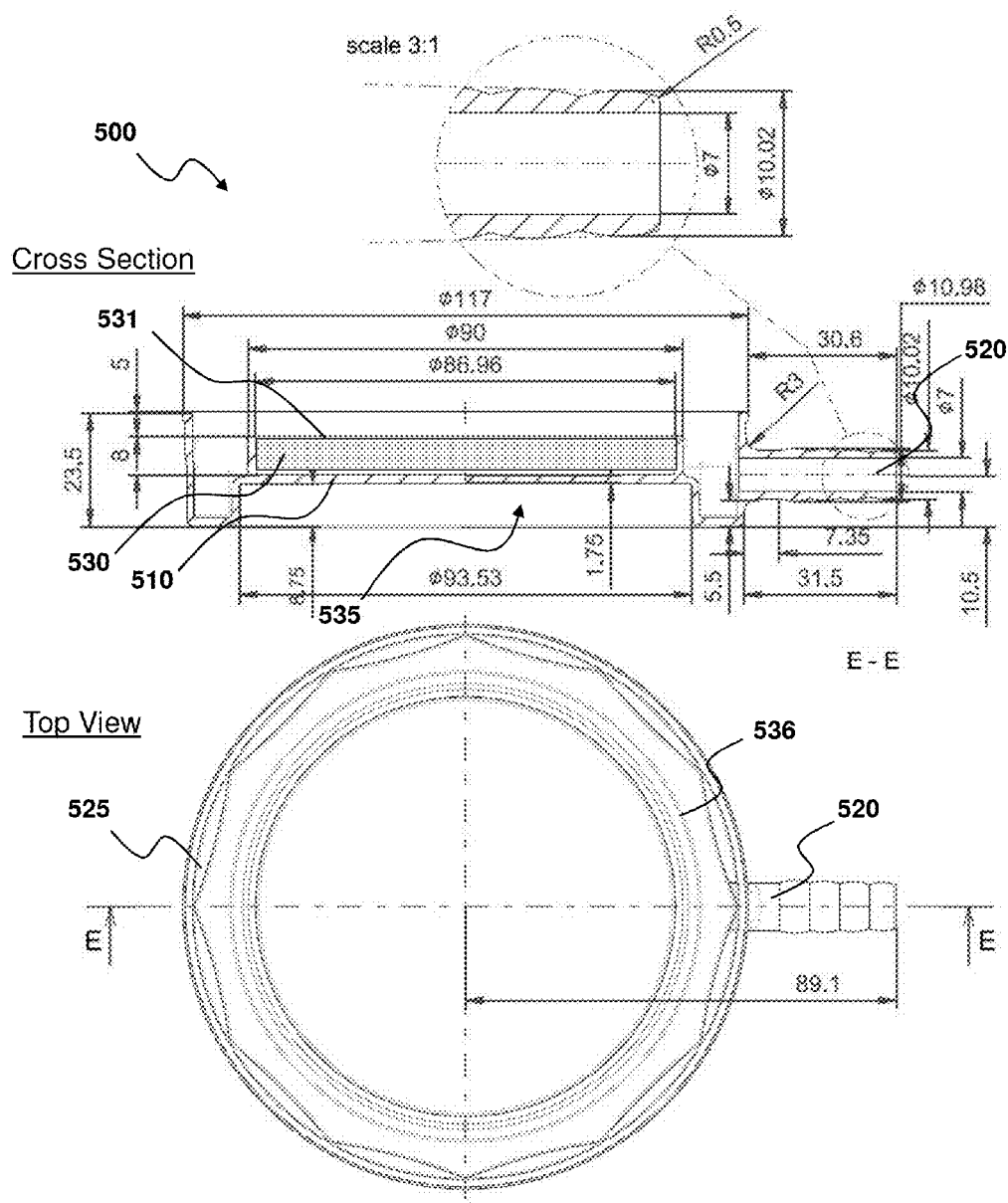
FIG. 7 provides a schematic providing a top view and cross sectional view of an impactor base of an impactor device of the invention.

FIG. 7 provides a schematic providing a top view and cross sectional view of an impactor base of an impactor device of the invention. As shown in this figure, impactor base 500 comprises outlet 520 and container 510 for containing a growth media 530. In some embodiment, container 510 is a petri dish for containing an agar growth media 530. In the embodiment shown in FIG. 7, an exposed surface 531 of the growth media 530 in container 510 provides an impact surface for receiving particles, including viable biological particles. Outlet 520 may be in fluid connection with a vacuum source, such as a pump, or house vacuum line so as to provide transport of fluid through the impactor. Impactor base 500 may further comprise planar surface elements 525 or grooves to facilitate handling and transfer of the impactor device. Impactor base 500 may further comprise one or more raised or recessed features 535 to facilitate stacking and transport of the impactor device, for example, including lip 536 allowing for an interlocking stack configuration of two impactors.

Figure 8:
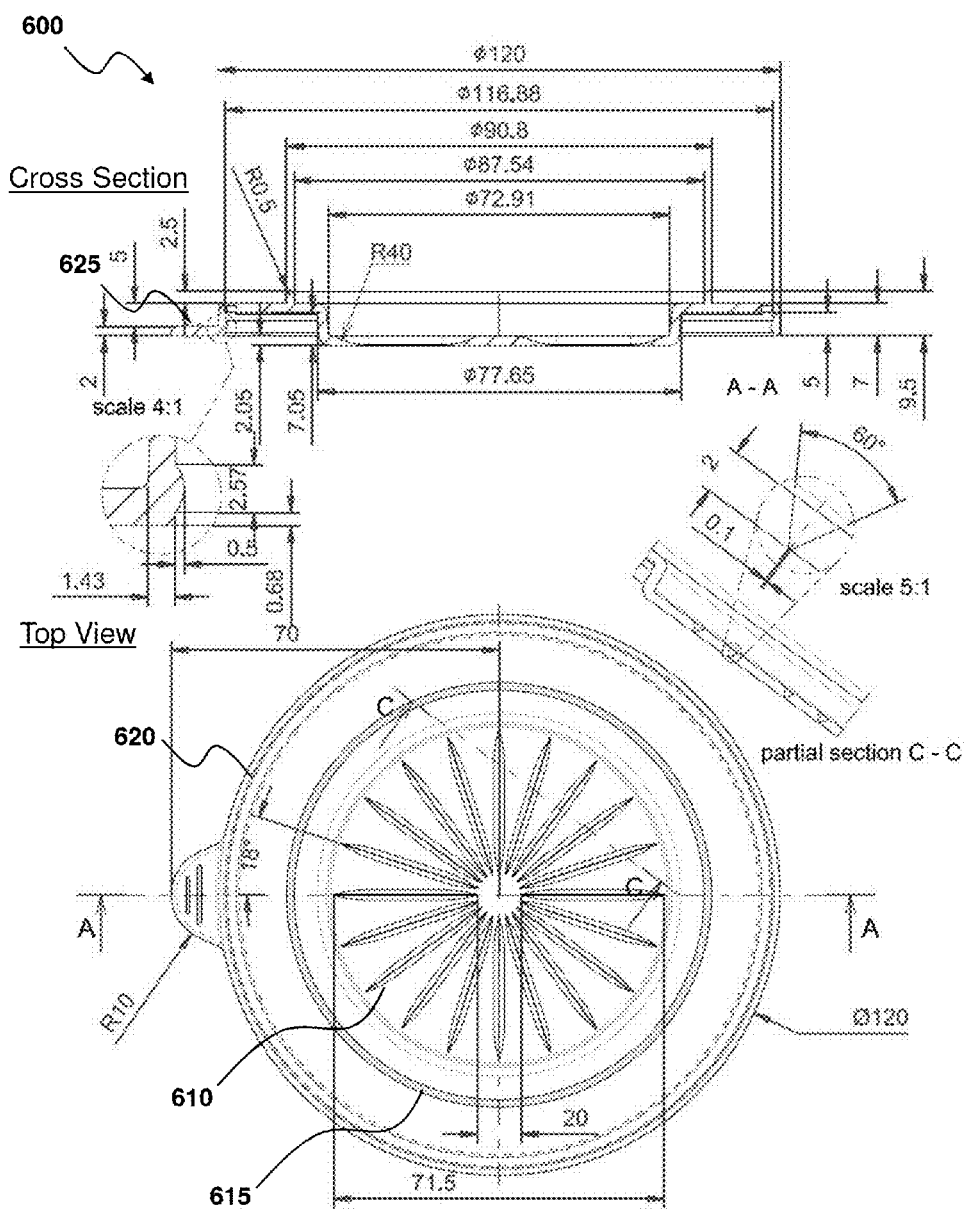
FIG. 8 provides a schematic providing a top view and cross sectional view of a sampling head of a device of the invention.

FIG. 8 provides a schematic providing a top view and cross sectional view of a sampling head of a device of the invention. As shown in this figure, sampling head 600 comprises intake apertures 610 for sampling a fluid flow containing biological particles. As shown in this figure, intake apertures 610 for this specific embodiment comprise a plurality of slits arranged in a circular pattern. As will be generally understood by one having skill in the art, the present devices are compatible with a broad range of shapes, sizes and patterns for intake apertures such as circular, square, rectangular, elliptical, triangular and combinations of these. O-ring seal 620 is also provided to provide for coupling of sampling head 600 and impactor base 500, for example, via an air tight seal. In such configurations, for example, impactor base 500 is provided with a receiving feature (e.g., a groove or flange surface) providing contact with the O-ring seal 620 when in an enclosed configuration. As shown in this figure, sampling head 600 comprises circular raised feature 615 configured to engage with cover 700 so as to enclose intake apertures 610, for example, before or after sampling particles. Optionally, sampling head 600 further comprises tab 625 to facilitate handing, such as to allow for disengagement of sampling head 600 and impactor base 500 in a manner minimizing the potential for contamination of growth media 530.

Figure 9:
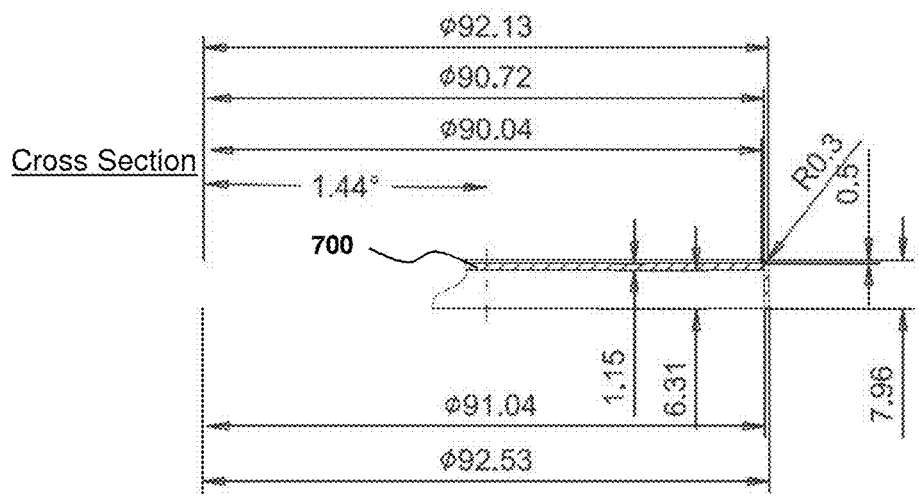
FIG. 9 provides a schematic providing a top view and cross sectional view of a cover for covering the intake apertures of a sample head of a device of the invention.
Figure 9:
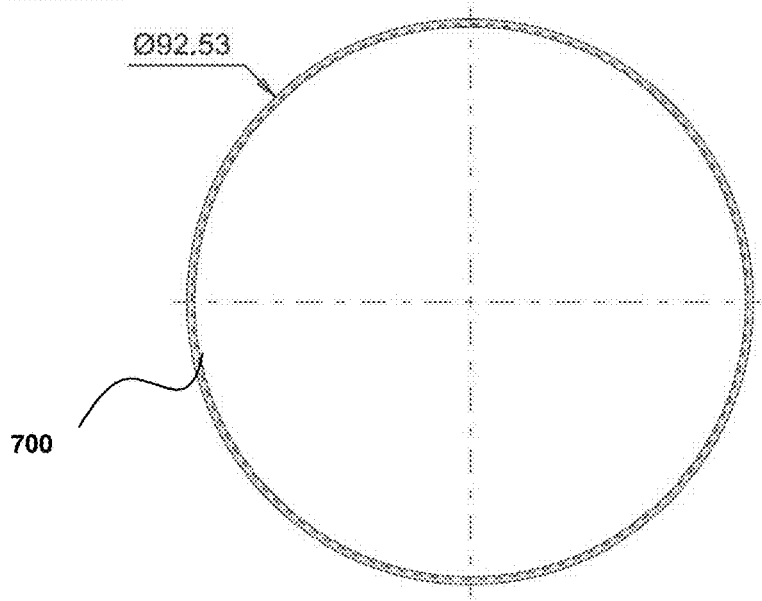

FIG. 9 provides a schematic providing a top view and cross sectional view of a cover 700 configured to engage sampling head 600, for example, so as to cover the intake apertures prior to or after sampling particles. In an embodiment, for example, cover 700 is configured to engage circular raised feature 615 of sampling head 600 so as to form a seal, such as a reversible seal. As will be readily understood by persons skilled in the art, cover 700 may be provided in a wide range of shapes including by way of example circular, rectangular, triangular, etc.

Figure 10B:
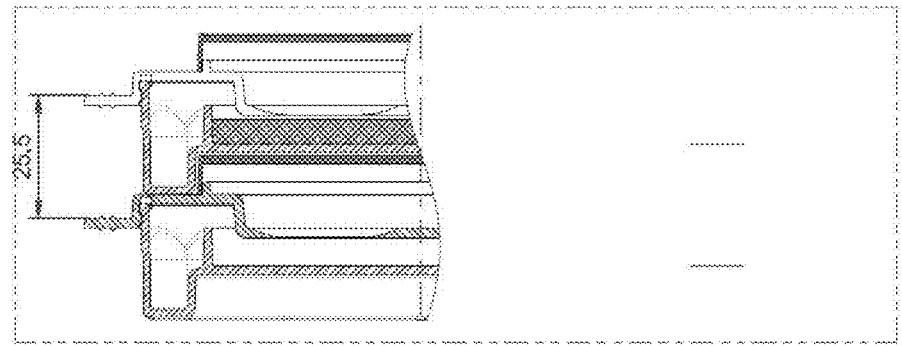
FIG. 10B provides a cross sectional view of two impactor devices of the invention provided in a stacked configuration.
Figure 10A:
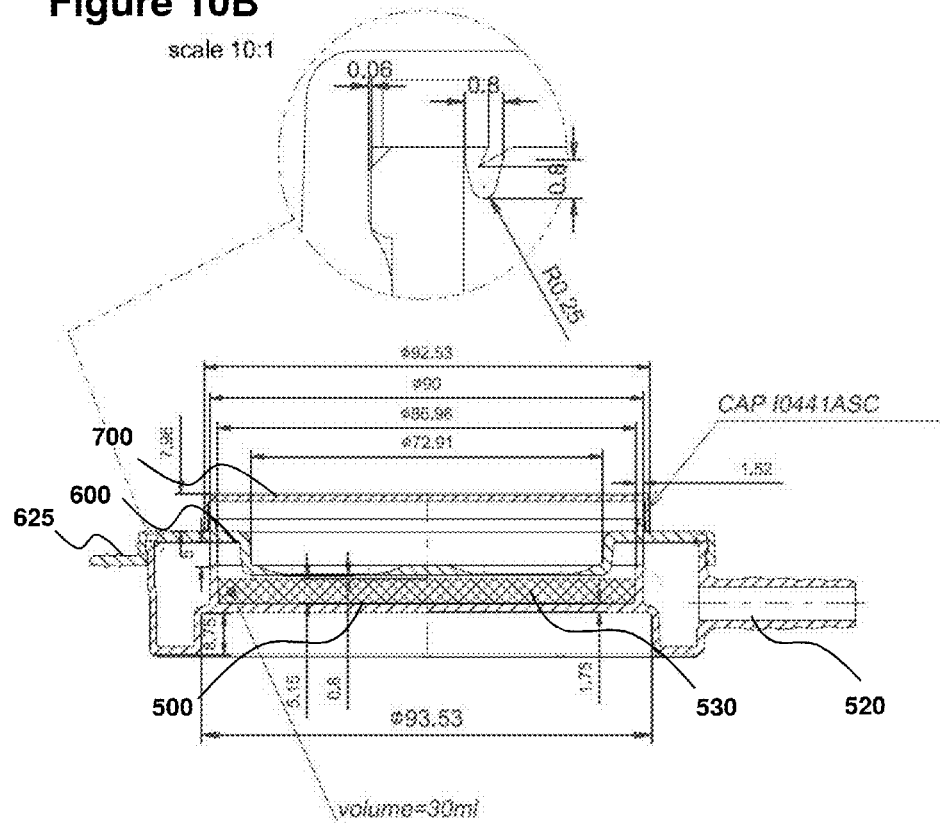
FIG. 10A provides a cross sectional view of an impactor device of the invention in an assembled configuration.
Figure 11:
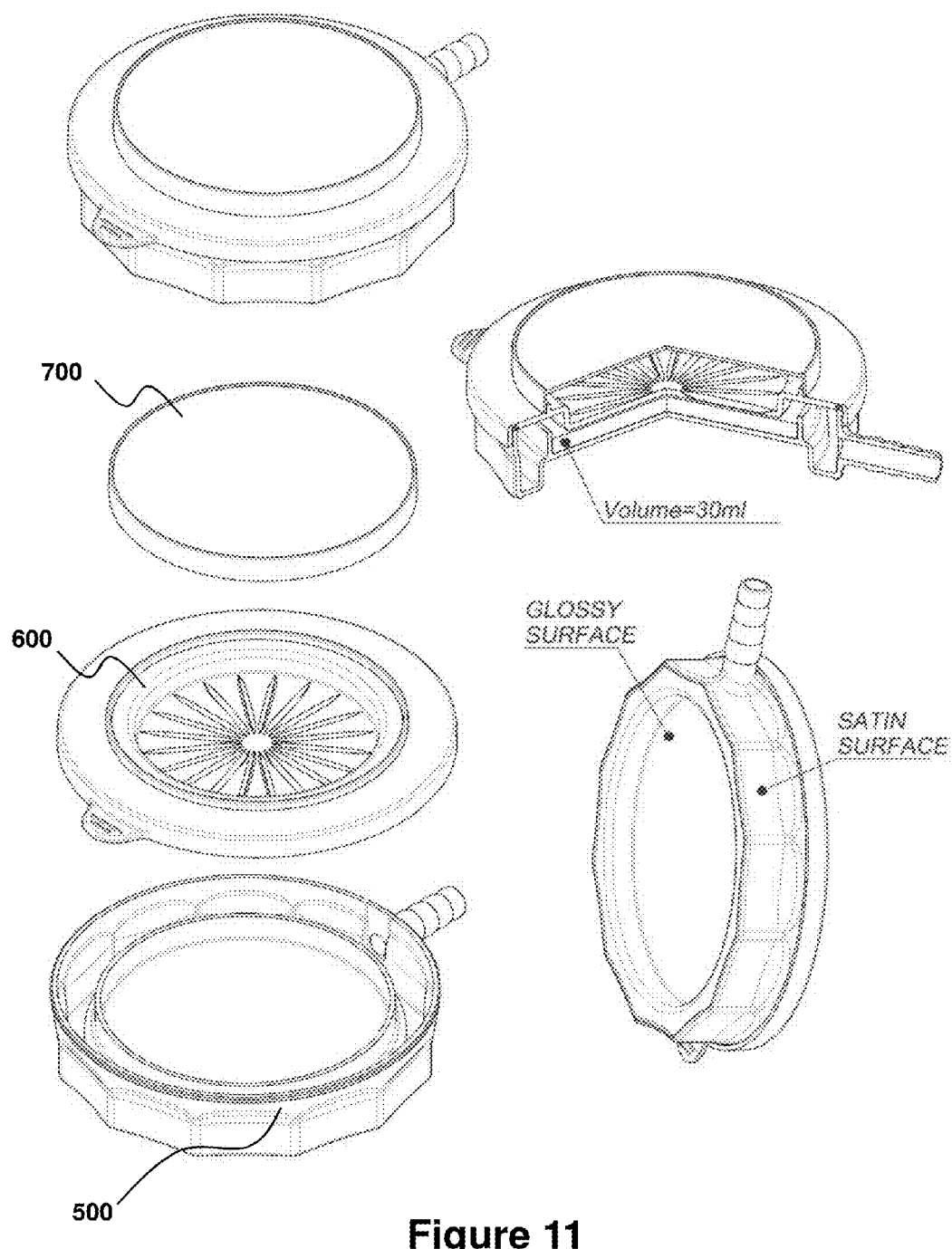
FIG. 11 provides exploded (bottom) and assembled (top) views of an impactor device of the invention.

FIG. 10A provides a cross sectional view of an impactor device of the invention in an assembled configuration. As show in FIG. 10A, sampling head 600 and impactor base 500 engage to enclose the impact surface of the growth media 530, for example, in a configuration allowing for sampling and growth of biological particles without disengagement. In an embodiment, for example, Sampling head 600 and impactor base 500 engage via an air tight seal, for example, provided by an 0-ring seal. In an embodiment, for example, sampling head 600 and impactor base 500 engage to enclose the impact surface of the growth media 530 in a configuration allowing the impactor to be sterilized in a fully assembled configuration. FIG. 10B provides a cross sectional view of two impactor devices of the invention provided in a stacked configuration. FIG. 11 provides exploded (bottom) and assembled (top) views of an impactor device of the invention.

FIG. 12 provides a flow diagram 1000 illustrating a method for sampling biological particles from a fluid flow, such as air or one or more process gases. The method includes a step 1002 of providing an impactor comprising a sampling head comprising one or more intake apertures for sampling a fluid flow containing particles and an impactor base operationally connected to receive at least a portion of the fluid flow from the sampling head. The impactor base comprises an impact surface for receiving at least a portion of the particles in the fluid flow and an outlet for exhausting the fluid flow, and the sampling head and the impactor base are integrated components that engage to enclose the impact surface. In an embodiment, a growth media, such as agar or a filter, is provided to the impactor base prior to engaging with the sampling head to provide the impact surface. In an embodiment, the growth media is provided in a growth media container that is a component of the impactor base, such as a Petri dish that is an integrated component of the impactor base. In optional step 1004, the impactor, for example including the growth media, may be sterilized in a fully assembled configuration wherein the impact surface remains enclosed by the sampling head and impactor base during sterilization. Sterilization may be achieved via a number of processing techniques including exposure to radiation, such as exposure to beta radiation, and/or raising the temperature. In step 1006, the fluid flow is sampled with the impactor, wherein particles in the fluid are received by the impactor surface. In an embodiment, for example, sampler head is configured to provide particles of a selected size distribution (e.g., greater than or equal to a threshold size) to the impact surface, for example, via momentum based size selection. Subsequently, in step 1008, at least a portion of the biological particles received by the impact surface are grown; wherein the growing step is carried out without disengaging the sampling head and the impactor base. In an embodiment, for example, growth of biological particles is achieved via incubation during an incubation time period. In an embodiment, a cover is provided to the sampler head after the step of generating the fluid flow through the device, for example, so as to enclose the intake apertures, thereby preventing additional particles from being received by the impact surface after the sampling period. Then optionally, in steps 1010 and 1012, viable biological particles received by the impact surface are detected and, optionally, at least a portion of the particles are optically characterized (e.g., number of colony forming units, type and/or species of microorganisms, etc.) in a configuration without disengaging the sampling head and the impactor base. In an embodiment, the impactor is a single use device, and thus, is discarded after detection and/or characterization of biological particles received by the impact surface. In an embodiment, the method further comprising providing an additional impactor and repeating the above-recited steps using the additional impactor, for example, to provide additional particle monitoring after discarding the initial impactor.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, and methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Every combination of components described or exemplified herein can be used to practice the invention, unless otherwise stated.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method for sampling biological particles from a fluid flow, said method comprising the steps of:
   sterilizing an impactor, said impactor comprising:
   a sampling head comprising one or more intake apertures for sampling said fluid flow containing said biological particles; and
   an impactor base operationally connected to receive at least a portion of said fluid flow from said sampling head; said impactor base comprising an impact surface positioned to receive at least a portion of said biological particles in said fluid flow and an outlet for exhausting said fluid flow, and said impactor base comprising a growth medium positioned to receive said particles in said fluid flow, wherein said impact surface is a receiving surface of said growth medium;
   a transparent selectively removable cover provided on said sampling head and covering said intake apertures;
   wherein said sampling head and said impactor base are integrated components that engage to enclose said impact surface, wherein at least a portion of said impactor base and said sampling head each comprise a polymer material and are optically transparent; and
   wherein said impactor is sterilized by irradiating the impactor in a fully assembled configuration, wherein said growth medium is present within the impactor base and is sterilized by the sterilizing step, and said selectively removable cover on said sampling head maintains a sterile environment for said growth medium prior to sampling said fluid flow containing particles;

removing said selectively removable cover on said sampling head;

sampling said fluid flow with said impactor, wherein said outlet is laterally adjacent to said impact surface and wherein a direction of the fluid flow changes by more than 40 degrees after passage through said one or more intake apertures;

growing at least a portion of said biological particles received by said growth medium until said biological particles are visible by eye or detectable using an optical detector or imaging device;

counting said grown particles visually or using an optical detector or imaging device; and characterizing at least a portion of said grown particles by visualization, optical detection or imaging and determining viability and identity of microorganisms in said grown particles;

wherein said sterilizing step, growing step, counting step, characterizing step, and determining step are carried out without disengaging said sampling head and said impactor base.

2. The method of claim 1 wherein said characterizing step further comprises determining the size of the biological particles received by said impact surface.

3. The method of claim 1 wherein said characterizing step is performed by said imaging device.

4. The method of claim 1, wherein the impactor base has a height of 22 mm to 24 mm and an area of 10,730 mm² to 10,760 mm².

5. The method of claim 4, wherein said growth medium is provided in a petri dish comprising an integrated component of said impactor base.

6. The method of claim 5, wherein said petri dish is cast in a single piece with the impactor base.

7. The method of claim 4, wherein said growth medium comprises an agar plate.

8. The method of claim 4, wherein said sampling head and said impactor base engage to entirely contain said impact surface.

9. The method of claim 1, wherein said method does not include a user physically contacting said growth medium after it has been contacted with said particles.

10. The method of claim 1, further comprising the step of repositioning said selectively removable cover on said sampling head for covering said intake apertures, thereby sealing said growth medium after said sampling step.

11. The method of claim 1, comprising sampling said fluid containing said particles using said impactor for a single use only.

12. The method of claim 1, comprising monitoring biological particles in cleanroom or aseptic environments.

13. The method of claim 1, comprising monitoring biological particles in air or one or more process gases.

14. The method of claim 1, further comprising repeating the steps of the method using a new sampler.

15. The method of claim 1, wherein said sampling head and said impactor base engage via a substantially airtight seal.

16. The method of claim 1, wherein said impactor base has a plurality of grooves provided on an outer surface to allow for effective handling of the impactor by a user.

17. The method of claim 1, wherein said impactor base has one or more recessed features to allow for effective stacking of a plurality of said impactors.

18. The method of claim 1, wherein said one or more intake apertures comprise a plurality of slits arranged in a circular pattern.

19. The method of claim 1, wherein said counting step is performed using an optical particle counter.

20. A method for sampling biological particles from a fluid flow, said method comprising the steps of:

providing an impactor comprising:
a sampling head comprising intake apertures for sampling a fluid flow containing particles, wherein said intake apertures comprise twenty slits arranged in a circular pattern, each slit having a width of 0.1 mm; and an impactor base operationally connected to receive at least a portion of said fluid flow from said sampling head; said impactor base comprising a support having an impact surface for receiving at least a portion of said particles in said fluid flow and an outlet for exhausting said fluid flow, wherein said impactor base has a height of 22 mm to 24 mm and an area of 10,730 mm² to 10,760 mm², and further comprises a growth medium positioned to receive said particles in said fluid flow and said support for accommodating the growth medium, wherein said impact surface is a receiving surface of said growth medium and said support has a height of 17 mm-19 mm and a volume of 20 ml-40 ml;

a transparent selectively removable cover provided on said sampling head and covering said intake apertures;

wherein said sampling head and said impactor base are integrated components that engage to enclose said impact surface, wherein at least a portion of said impactor base and said sampling head each comprise a polymer material and are optically transparent;

sterilizing said impactor in a fully assembled configuration by irradiating the fully assembled impactor using beta radiation wherein said impact surface remains enclosed by said sampling head and impactor base during sterilization, and wherein said growth medium is present within the impactor base and is sterilized by the sterilizing step, and said selectively removable cover on said sampling head maintains a sterile environment for said growth medium prior to sampling said fluid flow containing particles;

removing said selectively removable cover on said sampling head;

sampling said fluid flow with said impactor, wherein particles in said fluid are received by said impact surface, wherein said outlet is laterally adjacent to said impact surface and a direction of the fluid flow changes by more than 40 degrees after passage through said intake apertures; and growing at least a portion of said biological particles received by said growth medium until said biological particles are visible by eye or detectable using an optical detector or imaging device;

counting said grown particles visually or using an optical detector or imaging device; and characterizing at least a portion of said grown particles by visualization, optical detection or imaging and determining viability and identity of microorganisms in said grown particles;

wherein said sterilizing step, growing step, counting step, characterizing step, and determining step are carried out without disengaging said sampling head and said impactor base.

* * * * *